United States Patent
Bannister et al.

(10) Patent No.: US 10,624,556 B2
(45) Date of Patent: Apr. 21, 2020

(54) MEDICAL IMAGING SYSTEM AND METHOD

(71) Applicant: Micrima Limited, Bristol (GB)

(72) Inventors: Peter Romilly Bannister, Bristol (GB); Kevin Leslie Thomas, Bristol (GB)

(73) Assignee: Micrima Limited, Bristol (GB)

(*) Notice: Subject to any disclaimer, the term of this patent is extended or adjusted under 35 U.S.C. 154(b) by 0 days.

(21) Appl. No.: 16/302,344

(22) PCT Filed: May 17, 2017

(86) PCT No.: PCT/GB2017/051380
§ 371 (c)(1),
(2) Date: Nov. 16, 2018

(87) PCT Pub. No.: WO2017/199029
PCT Pub. Date: Nov. 23, 2017

(65) Prior Publication Data
US 2019/0290162 A1    Sep. 26, 2019

(30) Foreign Application Priority Data
May 17, 2016    (GB) .................................. 1608687.8

(51) Int. Cl.
*A61B 5/05*        (2006.01)
*A61B 90/00*     (2016.01)
*A61B 5/00*        (2006.01)

(52) U.S. Cl.
CPC .......... *A61B 5/0507* (2013.01); *A61B 5/4312* (2013.01); *A61B 5/6823* (2013.01);
(Continued)

(58) Field of Classification Search
CPC ... A61B 5/0507; A61B 5/4312; A61B 5/6823; A61B 90/39; A61B 90/37; A61B 2090/3908
See application file for complete search history.

(56) References Cited

U.S. PATENT DOCUMENTS

| | | | |
|---|---|---|---|
| 5,715,819 A * | 2/1998 | Svenson | A61B 5/05 600/425 |
| 2004/0167391 A1 * | 8/2004 | Solar | A61B 90/39 600/411 |

(Continued)

FOREIGN PATENT DOCUMENTS

DE    102009007255 A1    12/2009
JP    H08238227 A    9/1996
(Continued)

OTHER PUBLICATIONS

Search Report of UK Patent Office for Application GB1608687.8 dated Sep. 29, 2016.
(Continued)

*Primary Examiner* — Peter Luong
(74) *Attorney, Agent, or Firm* — Honigman LLP

(57) ABSTRACT

A medical imaging system and method is described. The system comprises: a microwave antenna array comprising a transmitting antenna and a plurality of receiving antennae, wherein the transmitting antenna is configured to transmit microwave signals so as to illuminate a body part of a patient and the receiving antennae are configured to receive the microwave signals following scattering within the body part; a marker configured to be applied to the surface of the skin of the body part and to scatter the microwave signals; a processor configured to process the scattered microwave signals and generate an image of the internal structure of the body part and the marker so as to identify a region of interest within the body part relative to the position of the marker.

26 Claims, 4 Drawing Sheets

(52) U.S. Cl.
CPC .............. *A61B 90/39* (2016.02); *A61B 90/37* (2016.02); *A61B 2090/397* (2016.02); *A61B 2090/3908* (2016.02); *A61B 2090/3937* (2016.02); *A61B 2090/3954* (2016.02); *A61B 2090/3995* (2016.02)

(56) References Cited

U.S. PATENT DOCUMENTS

| | | | |
|---|---|---|---|
| 2006/0058606 A1 | 3/2006 | Davis et al. | |
| 2006/0084867 A1* | 4/2006 | Tremblay | A61B 90/36 600/434 |
| 2008/0071169 A1 | 3/2008 | Craddock et al. | |
| 2009/0281419 A1 | 11/2009 | Troesken et al. | |
| 2011/0105896 A1* | 5/2011 | Zagorchev | A61B 6/508 600/426 |
| 2013/0204126 A1* | 8/2013 | Namati | A61B 8/12 600/427 |
| 2015/0371380 A1 | 12/2015 | Meaney et al. | |
| 2016/0066811 A1 | 3/2016 | Mohamadi | |

FOREIGN PATENT DOCUMENTS

| | | |
|---|---|---|
| JP | 3128904 B2 | 1/2001 |
| JP | 2001511691 A | 8/2001 |
| JP | 2010246667 A | 11/2010 |
| JP | 2012531276 A | 12/2012 |
| RU | 2578298 C1 | 3/2016 |
| WO | 9838919 A2 | 9/1998 |
| WO | 2005084544 A1 | 9/2005 |
| WO | 2009060182 A1 | 5/2009 |
| WO | WO-2010143691 A1 | 12/2010 |
| WO | 2011064577 A1 | 6/2011 |
| WO | WO-2013168622 A1 | 11/2013 |
| WO | 2014149183 A2 | 9/2014 |

OTHER PUBLICATIONS

International Search Report for Application PCT/GB2017/051380 dated Aug. 22, 2017.
International Preliminary Report on Patentability for Application PCT/GB2017/051380 dated Apr. 26, 2018.
Office Action for Japanese Application No. 2018-560110 dated Nov. 12, 2019 along with English translation.

* cited by examiner

MEDICAL IMAGING SYSTEM AND METHOD

RELATED APPLICATIONS

This application claims priority to Application PCT/GB2017/051380 filed on May 17, 2017 which claims priority from Application 1608687.8 filed on May 17, 2016 in the United Kingdom. The entire contents of these applications are incorporated herein by reference in their entirety.

TECHNICAL FIELD

The invention relates to a medical imaging system and method.

BACKGROUND

Breast cancer is the most common cancer in women. X-ray mammography is currently the most effective detection technique and is used for screening, however it suffers from relatively high missed- and false-detection rates, involves uncomfortable compression of the breast and also entails exposure to ionizing radiation.

Microwave imaging and detection of breast tumors is a potential non-ionizing alternative. One such approach is to employ a densely packed conformal antenna array, which also stabilizes the breast position with a minimum of coupling fluid.

The invention seeks to provide additional functionality to a microwave imaging system.

SUMMARY

In accordance with an aspect of the invention, there is provided a medical imaging system comprising: a microwave antenna array comprising a transmitting antenna and a plurality of receiving antennae, wherein the transmitting antenna is configured to transmit microwave signals and the receiving antennae are configured to receive the microwave signals following scattering; a marker configured to scatter the microwave signals; and a processor configured to process the scattered microwave signals and generate an image of the marker.

The marker may be a passive antenna having a resonant slot.

The marker may be formed of a metal foil which conforms to the shape of the body part.

The marker may be a non-linear antenna which scatters the microwave signal at a frequency which is different to the frequency of the received microwave signal.

The non-linear antenna may be a harmonic antenna.

The marker may comprise a contrast agent.

The transmitting antenna may be configured to transmit microwave signals so as to illuminate a body part of a patient and the receiving antennae may be configured to receive the microwave signals following scattering within the body part. The marker may be configured to overlie the surface of the skin of the body part. The processor may be configured to process the scattered microwave signals and generate an image of the internal structure of the body part and the marker so as to identify a region of interest within the body part relative to the position of the marker.

The processor may be configured to calibrate the medical imaging system based on the marker. The processor may be configured to calibrate the medical imaging system based on the scattering characteristics of the marker. For example, based on a known reference scattering response from the marker it may be possible to calibrate or adjust the measured scattering from the body part. The scattering characteristics could be brightness, intensity, spectrum (e.g. color), and directionality.

The marker may be configured to be applied to the surface of the skin. The marker may be provided with an adhesive for adhering the marker to the surface of the skin. The marker may be provided with a backing material, such as a non-porous layer. This may prevent skin moisture from affecting the dielectric properties of the marker.

The marker may be attached to a component which is arranged to be fixed in position. The component may comprise a cup or insert, for example. The marker could be adhered to or otherwise attached to the component. For example, it could be embedded within the component. The component may be configured to be in contact with at least a portion of a body part. The component may be configured to receive at least a portion of a body part.

In accordance with another aspect there is provided a medical imaging method comprising: providing a marker w; illuminating the marker with microwave signals emitted by a transmitting antenna of a microwave antenna array; receiving the microwave signals following scattering by the marker at a plurality of receiving antennae of the microwave antenna array; processing the scattered microwave signals to generate an image of the marker.

The method may further comprise performing image registration between a plurality of images by correlating the position of the marker in each image.

The images may be produced using different imaging modalities.

The method may further comprise adjusting the spatial image reconstruction to correct for spatial distortion by comparing the position of the marker within the image with its known reference position.

The method may further comprise adjusting reconstruction parameters based on a known reference position of the marker.

The marker may be provided such that it overlies the surface of the skin of a body part of a patient. The marker and the body part may be illuminated with microwave signals, Microwave signals may be received following scattering within the body part and by the marker. The scattered microwave signals may be processed to generate an image of the body part showing an internal structure of the body part and the marker so as to identify a region of interest within the body part relative to the position of the marker.

The images may be taken at different instances by reapplying the marker to the same position on the skin.

The method may further comprise using the known scattering characteristics of the marker as a reference to adjust the measured scattering from the body part.

The marker may be affixed to the surface of the skin. The marker may be adhered to the surface of the skin.

The method may further comprise calibrating a medical imaging system based on the marker. The method may further comprise calibrating the medical imaging system based on the scattering characteristics of the marker.

The marker may be attached to a component which is fixed in position. The component may comprise a cup. At least a portion of the body part may be received within the cup.

BRIEF DESCRIPTION OF THE DRAWINGS

For a better understanding of the invention, and to show more clearly how it may be carried into effect, reference will now be made, by way of example, to the accompanying drawings, in which:—

DETAILED DESCRIPTION

Figure 1:
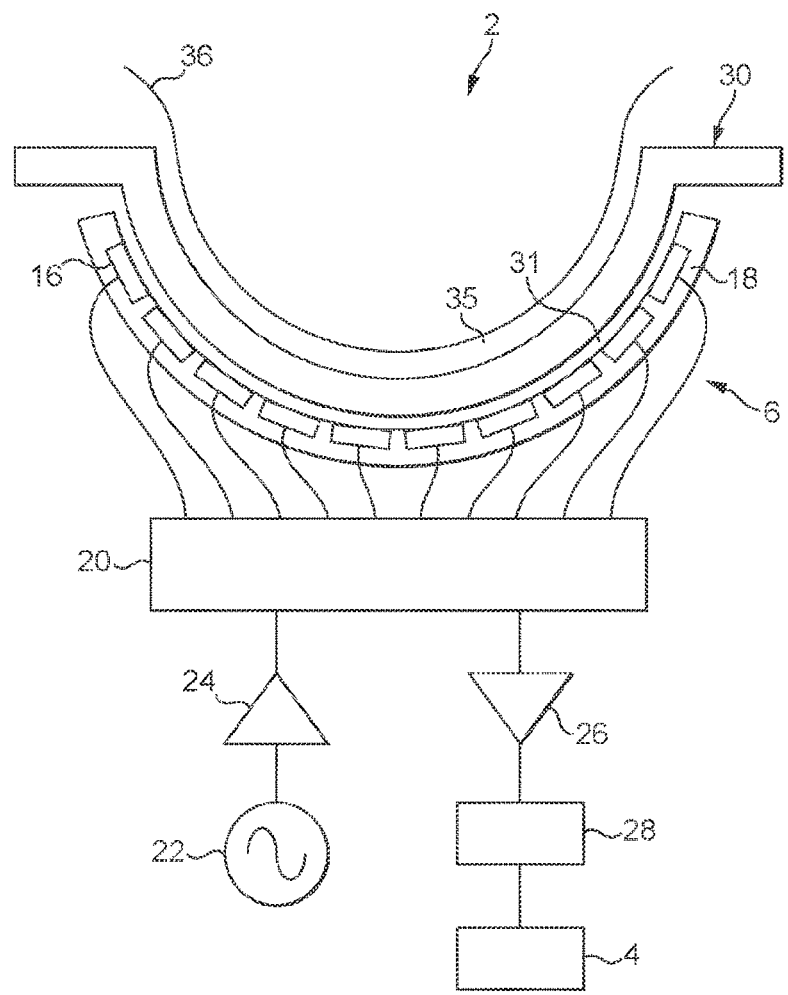
FIG. 1 is a schematic view of a medical imaging system.

FIG. 1 shows a medical imaging system 2 which comprises a microwave antenna array 6. The antenna array 6 comprises a plurality N of antennae 16 which are arranged over the surface of, or within, a shell substrate 18. The shell 18 has a curved profile as shown. In particular, the shell 18 is part or hemi-spherical and is configured to approximate the shape of a breast. The antennae 16 are arranged over the shell 18 such that they all point to a common focal point.

The antennae 16 are each electrically connected to a switching matrix 20. The switching matrix 20 is in turn connected to both a transmit path and a receive path. The transmit path comprises a signal generator 22 coupled to an amplifier 24. The receive path comprises an amplifier 26 coupled to a detector 28 and a processor 4.

The switching matrix 20 selectively couples each of the antennae 16 to either the transmit path or the receive path.

The antenna array 6 is operated in a multi-static fashion. Specifically, the switching matrix 20 is controlled so as to connect one of the antennae 16 to the transmit path and the remaining antennae 16 to the receive path. The signal generator 22 generates a stepped frequency continuous wave (CW), Ultra Wide-Band (UWB) signal which is amplified by the amplifier 24 and then transmitted by the antenna 16 connected to the transmit path. The stepped frequency continuous wave signal is a sequential series of pulses of continuous wave energy, where each pulse has its frequency stepped up across a range of frequencies, typically within the 3-8 GHz range. The other antennae 16 receive the transmitted signal and the received signal is detected and then recorded by the processor 4.

The shell 18 receives a cup 30. The cup 30 has a complementary shape to the shell 18 such that if fits snugly within the shell 18.

The outside of the cup 30 and the inside of the shell 18 may have threaded portions to enable a threaded engagement between the cup 30 and the shell 18. The threaded engagement between the cup 30 and the shell 18 may be used to translate the antenna array 6 relative to the breast 36, as described previously.

A layer of coupling fluid (dielectric constant controlled fluid) may be inserted in the gap 31 between the shell 18 and the cup 30 so as to improve the coupling between the antennae 16 and the cup 30 in order to minimize signal loss and thus improve transmission of the microwave signal.

In use, a patient lies in a prone position such that their breast 36 sits in the cup 30. A layer of coupling fluid may also be provided in the gap 35 between the cup 30 and the breast 36 in order to improve coupling between the antennae 16 and the breast 36.

Although not shown, one or more inserts may be placed inside the cup 30 so as to enable a better fit between the internal surface of the cup 30 and the breast 36. For example, a plurality of such inserts may be provided, each having different shapes and sizes, to enable the system to be better adapted to breasts of different shapes and sizes. The inserts may be made from the same material as the cup (e.g. ceramic).

The antenna 16 connected to the transmit path illuminates the breast 36 with the microwave signal. The signal is scattered by the breast tissue and the scattered signal is received at each of the non-transmitting antennae 16 where it is detected and recorded. This process is repeated for each antenna 16, as described previously.

The processor 4 may record the relative difference between the measured phase and amplitude of the transmitted signal as compared to the phase and amplitude of the scattered signal, recorded as a complex number (having real and imaginary parts).

The signal detected at each antenna 16 will generally comprise three components: a component arising from mutual coupling between the transmitting and receiving antennas 16; a component arising from radiation which reflects off the skin of the breast 36; and a component arising from radiation which reflects off structures within the breast (such as tumors). Tumors can generate identifiable reflections as they exhibit much higher dielectric properties than adipose tissues due to their significant water content. The mutual and skin reflection components may be removed or at least mitigated from the data set in order to improve the detectability of reflections resulting from the presence of tumors within the breast.

The acquired data set may be used by the processor 4 to construct an image of the internal structure of the breast 36. Data reconstruction may be performed using Phased Array (frequency domain), Delay and Sum (DAS—time domain) techniques or any other suitable technique. From this, the processor 4 is able to identify (possibly, with additional user input or confirmation) a region of interest (if present) in which a possible tumor or other pathology may exist.

The precise position of the breast within the antenna array 6 and insert is likely to vary each time the breast is imaged due to variations in the fitting procedure. The positional relationship between the array 6 and the anatomy of the breast cannot usually be readily determined since there is no direct optical access to the array 6. This also makes it difficult to make a visual comparison between imaging modalities for the purposes of breast screening, cancer diagnosis (including image guided biopsy), tumor staging, treatment monitoring and surgical planning.

Figure 2:
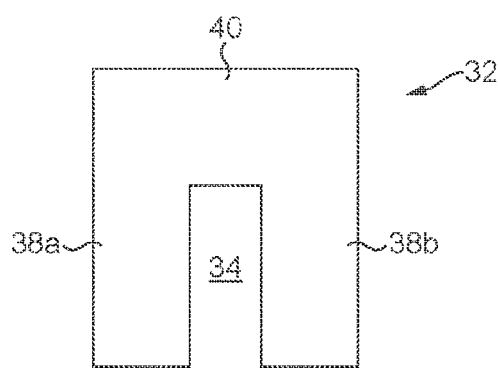
FIG. 2 is a front view of a marker for use with the medical imaging system.

A marker 32, as shown in FIG. 2, may be used to provide registration between the breast 36 and the array 6. The marker 32 may be formed by a rectangular sheet of thin aluminum foil with a resonant slot 34 extending into the body of the marker 32 midway along one of the sides. The marker 32 therefore has a substantially C or U-shaped profile formed by a pair of legs 38*a*, 38*b* either side of the resonant slot 34 and a base portion 40 joining the legs 38*a*, 38*b*.

In an example, the marker 32 may have a width of 5.5 mm across the base portion 40 and a length of 9 mm. The resonant slot 34 may have a length of 5.5 mm (the length of the legs 36*a*, 36*b*) and a width of 1.5 mm such that the legs 38*a*, 38*b* each have a width of 2 mm.

In another example, the marker 32 may have a width of 8.0 mm across the base portion 40 and a length of 9 mm. The resonant slot 34 may have a length of 4.5 mm (the length of the legs 38*a*, 38*b*) and a width of 1.5 mm such that the legs 38*a*, 38*b* each have a width of 3.25 mm.

The ratio of the length of the resonant slot 34 to the length of the marker 32 may be approximately 0.5-0.7. The ratio of the width of the resonant slot 34 to the width of the marker 32 may be approximately 0.1-0.3. However, other dimensions may be used.

Figure 3:
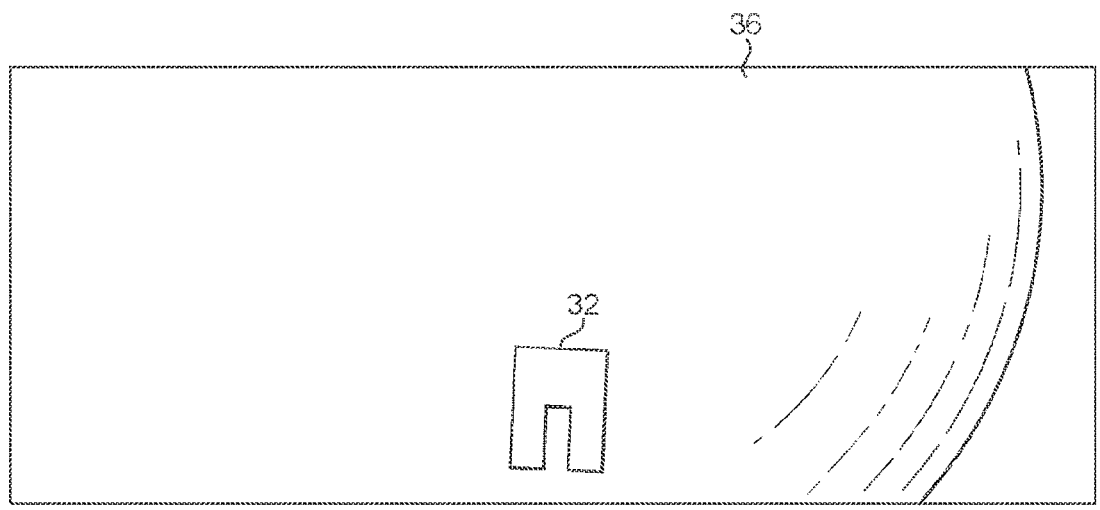
FIG. 3 is a front view of the marker affixed to a model of a breast.

As shown in FIG. 3, the marker 32 is affixed to the surface of the skin of the breast 36. The marker 32 may be affixed to the skin using any suitable medical adhesive or the like. The thin aluminum foil of the marker 32 is able to conform to the contours of the breast and so has a low-profile enabling it to fit against the array 6. The aluminum foil used for the marker 32 is both low cost and hypo-allergenic. In another arrangement, as opposed to attaching the marker 32 directly to the skin, the marker 32 is fixed to the cup 30 or the insert. This may allow the marker 32 to be in a fixed, known position, which may assist in the calibration of the system 2. If the marker 32 is attached to the cup 30 or the insert, in use, the marker 32 may overlie the skin without being in direct contact with the skin. The marker 32 could be adhered to an inner or outer surface of the cup 30 or insert, or it could be embedded within the cup 30 or insert substrate.

The marker 32 exhibits well defined microwave scattering characteristics such that it can be distinguished from the tissue of the breast 36. The dimensions of the resonant slot 34 may be configured to provide the marker 32 with resonant properties within the UWB region which provides for an enhanced radar cross-section at a particular frequency while having a reduced cross-section outside the resonant region. A range of markers 32 could also be fabricated with different resonant frequencies so as to allow them to be distinguished from one another.

Figure 4:
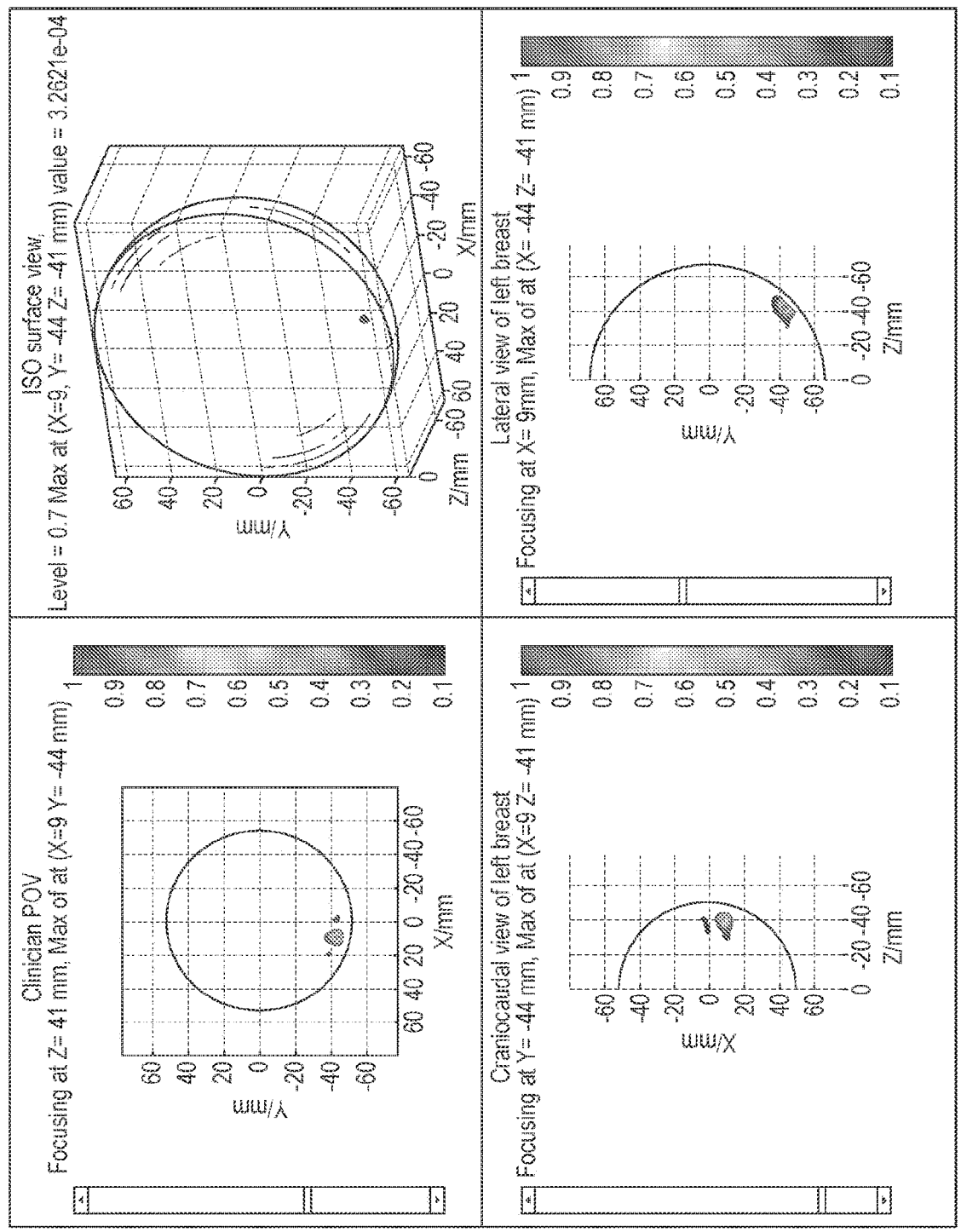
FIG. 4 shows image plots from various directions for the model of the breast.

As shown in FIG. 4, the position of the marker 32 is easily identifiable in the images of the breast 36 generated by the system.

The marker 32 described above is a passive marker which provides a linear response to the microwave signal. In other words, the signal scattered/reflected by the marker 32 and received by the antennae 16 generally has the same frequency as the signal transmitted by the antennae 16. The response of the marker 32 is therefore similar to the tissue of the breast 36 which is a generally linear medium.

Figure 5:
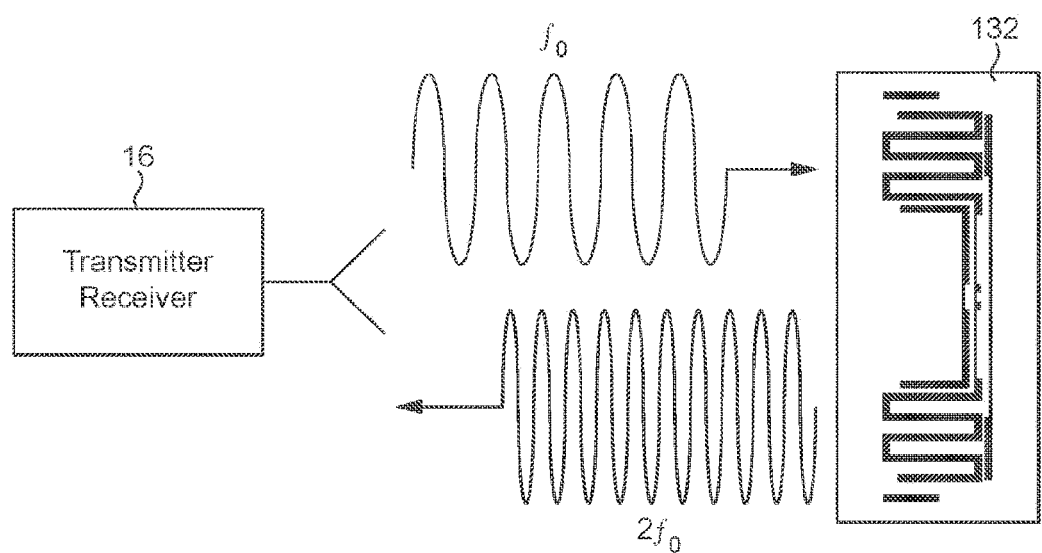
FIG. 5 is a schematic view of another example of a marker.

FIG. 5 shows an example of a non-linear marker 132. The marker 132 may be a harmonic transponder formed by an antenna coupled to a diode, such as a Schottky diode.

The marker 132 receives the microwave signal at a certain fundamental frequency and converts this signal to a harmonic response signal at frequency that is an integer multiple of the fundamental frequency. In particular, the harmonic response signal may be the second harmonic frequency which provides optimum conversion efficiency. The diode of the marker 132 therefore effectively serves as a frequency doubler.

Other forms of non-linear transponder may also be used in which the response signal is modified through nonlinearities in the transponder. Active markers that contain an integrated circuit and/or power source may also be used which generate more complex scattering responses.

The use of a non-linear marker allows the marker to be easily distinguished from other scattering sources. This therefore provides improved performance when in the presence of strong environmental clutter. For example, if the marker simply responds back at the interrogation frequency in an environment with strong clutter, its response could be obscured by reflections. By using a non-linear response signal, it is easier to conclude that the observed response is caused by the marker rather than the surroundings. This is due to the fact that most natural objects do not display nonlinear properties at typical power levels used in microwave radar and therefore are not able to reflect back at frequencies which are different to the incoming frequency.

The use of one or more markers during the imaging process enables the image data to be easily related to the actual anatomy of the patient after imaging has taken place. This may be particularly useful where the images are used for subsequent breast biopsy or surgery with the markers on the skin of the breast providing guidance.

The marker(s) may be attached to the patient in standardized and predefined positions which will allow the physician to relate the visual position of the marker to the imaged position of the marker and the imaged positions of associated structures within the patient so that the physician can visualize the position of these structures by referring to the visual localization marker.

The marker(s) may be located in standardized and well-defined position(s) such that images taken at different times can be compared against one another. The markers may be returned to the same positions for each image using a digital imaging system.

The marker(s) may be identifiable in additional, complementary imaging modalities beyond microwave imaging. In particular, the marker(s) may be utilized also during Magnetic Resonance Imaging (MRI). The different imaging techniques may be used to refine the diagnosis of a lesion. It will be appreciated that the position of the breast in such other imaging modalities may be very different and the use of common markers which can be viewed in each modality thus provides registration between the images.

The marker may incorporate a contrast agent sealed within a chamber in a container formed from a solid material. The contrast agent is selected to produce a change in signal intensity under MRI. The contrast agent may also be directly visible by microwave radar. Alternatively, an additional marker may be sealed within the chamber to provide visibility to microwave radar imaging.

The markers may also be compatible with other modalities, including, for example, X-rays, computed tomographic (CT) X-ray imaging, ultrasound, electrical impedance tomography (EIT), magnetic source imaging (MSI), magnetic resonance spectroscopy (MRS), magnetic resonance mammography (MRM), magnetic resonance angiography (MRA), magnetoelectro-encephalography (MEG), laser optical imaging, electric potential tomography (EPT), and nuclear medicine modalities such as positron emission tomography (PET) and single photon emission computed tomography (SPECT).

The electromagnetic properties of the marker are stable over time and are accurately quantified. This enables the marker to act as a reference in the microwave imaging system without the requirement to use a phantom. Microwave scattering parameter data can change over time due to electronics drift, change in switching characteristics and cable effects and the use of the marker as a reference marker thus allows these changes to be accounted for.

Microwave scattering parameter data that includes a reference marker can be used to create quantitative data sets relating to breast dielectric properties rather than relative normalized values. Quantitative data sets can be compared over time to observe changes in the breast for screening and for monitoring neoadjuvant therapy.

The quality of image reconstruction is also dependent on certain assumptions and system parameters that can change over time. A reference marker or markers can be used to improve the quality of image reconstruction, for example focusing, as the marker has known scattering characteristics, size and position relative to the conformal antenna array 6.

The radar cross-section of the reference markers may be configured so that they shine at a predefined brightness. This allows a reference level of scattering to be defined within the image, so that other images can be defined in their brightness by comparison with the reference marker. The reference markers can therefore provide a quantifiable measure for clutter reduction in the obtained images. Markers can be designed with specific known RF scattering characteristics, and so can provide standard references to quantify and adjust measured scattering by comparison against the references. 'RF scattering characteristics' may include brightness, spectrum (color), and directionality. In one embodiment, the medical imaging system may image the marker without a body part. The image of the marker may be used to calibrate the medical imaging system. For example, if the marker has a known characteristic (e.g. a known brightness) then subsequently the measured scattering of microwave signals by a body part may be corrected or adjusted based on the known response of the marker.

Markers can be placed at known spatial positions, and so can provide spatial reference points against which the spatial image reconstruction can be adjusted by comparing the reconstructed marker position against the known reference position in order to correct for spatial distortion.

Markers can be placed at known spatial positions and so can provide spatial reference points against which reconstruction parameters including for instance refractive index may be adjusted to optimally focus (autofocus). The process of autofocus by adjusting reconstruction parameters also provides estimates of those actual parameters, thus providing an extra measurement.

Although the system has been described with reference to the imaging of a breast, it will be appreciated that it may be adapted for other areas of the body.

In other arrangements, the cup of the antenna array may be dispensed with or integrated into the shell in which the antennae are located.

The system may employ multiple transmit and receive paths, such that data can be recorded from multiple antennas simultaneously, and may even comprise a number of transmit and receive paths corresponding to the number of antennas, such that data can be recorded from all antennas simultaneously. In an alternative topology, the switching matrix could be removed thus allowing each antenna to be connected to a transmitting/receiving device.

Alternatively, more than one antenna may be operated at a time in a frequency multiplexed operation. Multiplexed operation may have significant advantages where high speed tracking of the needle is required.

To avoid unnecessary duplication of effort and repetition of text in the specification, certain features are described in relation to only one or several aspects or embodiments of the invention. However, it is to be understood that, where it is technically possible, features described in relation to any aspect or embodiment of the invention may also be used with any other aspect or embodiment of the invention.

The invention is not limited to the embodiments described herein, and may be modified or adapted without departing from the scope of the present invention.

The invention claimed is:

1. A medical imaging system comprising:
   a microwave antenna array comprising a transmitting antenna and a plurality of receiving antennae, wherein the transmitting antenna is configured to transmit microwave signals so as to illuminate a body part of a patient and the receiving antennae are configured to receive the microwave signals following scattering within the body part;
   a marker configured to overlie the surface of the skin of the body part and to scatter the microwave signals, wherein the marker is a non-linear antenna which scatters the microwave signals at a frequency which is different to the frequency of the microwave signals received at the marker; and
   a processor configured to generate an image of the internal structure of the body part and the marker by processing the scattered microwave signals so as to identify a region of interest within the body part relative to the position of the marker.

2. A medical imaging system as claimed in claim 1, wherein the marker is formed of a metal foil which conforms to the shape of the body part.

3. A medical imaging system as claimed in claim 1, wherein the non-linear antenna is a harmonic antenna.

4. A medical imaging system as claimed in claim 1, wherein the marker comprises a contrast agent.

5. A medical imaging system according to claim 1, wherein the processor is configured to calibrate the medical imaging system based on the marker.

6. A medical imaging system according to claim 5, wherein the processor is configured to calibrate the medical imaging system based on the scattering characteristics of the marker.

7. A medical imaging system according to claim 1, wherein the marker is configured to be applied to the surface of the skin.

8. A medical imaging system according to claim 7, wherein the marker is provided with an adhesive for adhering the marker to the surface of the skin.

9. A medical imaging system according to claim 1, wherein the marker is attached to a component which is arranged to be fixed in position.

10. A medical imaging system according to claim 9, wherein the component comprises a cup.

11. A medical imaging system according to claim 9, wherein the component is configured to be in contact with at least a portion of a body part.

12. A medical imaging system according to claim 9, wherein the component is configured to receive at least a portion of a body part.

13. A medical imaging method comprising:
   providing a marker such that it overlies the surface of the skin of a body part;
   illuminating the marker and the body part with microwave signals emitted by a transmitting antenna of a microwave antenna array;
   receiving the microwave signals following scattering within the body part and by the marker at a plurality of receiving antennae of the microwave antenna array, where the marker is a non-linear antenna which scatters the microwave signals at a frequency which is different to the frequency of the microwave signals received at the marker; and
   generating an image of the body part showing an internal structure of the body part and the marker by processing the scattered microwave signals, so as to identify a region of interest within the body part relative to the position of the marker.

14. A medical imaging method as claimed in claim 13, further comprising: performing image registration between a plurality of images by correlating the position of the marker in each image.

15. A medical imaging method as claimed in claim 14, further comprising generating an image of the marker using a different imaging modality including at least one of: X-rays, computed tomographic (CT) X-ray imaging, ultrasound, electrical impedance tomography (EIT), magnetic source imaging (MSI), magnetic resonance spectroscopy (MRS), magnetic resonance mammography (MRM), magnetic resonance angiography (MRA), magnetoelectro-encephalography (MEG), laser optical imaging, electric potential tomography (EPT), and nuclear medicine modalities such as positron emission tomography (PET) and single photon emission computed tomography (SPECT).

16. A medical imaging method as claimed in claim 13, further comprising adjusting spatial image reconstruction to correct for spatial distortion by comparing a position of the marker within the image with a known reference position of the marker.

17. A medical imaging method as claimed in claim 13, wherein the marker has a known reference position, the medical imaging method further comprising adjusting reconstruction parameters based on the known reference position of the marker.

18. A medical imaging method as claimed in claim 17, wherein the images are taken at different instances by reapplying the marker to the same position on the skin.

19. A medical imaging method as claimed in claim 17, further comprising using the known scattering characteristics of the marker as a reference to adjust the measured scattering from the body part.

20. A medical imaging method according to claim 13, further comprising calibrating a medical imaging system based on the marker.

21. A medical imaging method according to claim 20, further comprising calibrating the medical imaging system based on the scattering characteristics of the marker.

22. A medical imaging method according to claim 13, wherein the marker is attached to a component which is fixed in position.

23. A medical imaging method according to claim 22, wherein the component comprises a cup.

24. A medical imaging method according to claim 23, wherein at least a portion of the body part is received within the cup.

25. A medical imaging system comprising:
a microwave antenna array comprising a transmitting antenna and a plurality of receiving antennae, wherein the transmitting antenna is configured to transmit microwave signals so as to illuminate a body part of a patient and the receiving antennae are configured to receive the microwave signals following scattering within the body part;
a marker configured to overlie the surface of the skin of the body part and to scatter the microwave signals; and
a processor configured to generate an image of the internal structure of the body part and the marker by processing the scattered microwave signals so as to identify a region of interest within the body part relative to the position of the marker,
wherein the marker is a passive antenna having a resonant slot.

26. A medical imaging method comprising:
providing a marker such that it overlies the surface of the skin of a body part, wherein the marker is a passive antenna having a resonant slot;
illuminating the marker and the body part with microwave signals emitted by a transmitting antenna of a microwave antenna array;
receiving the microwave signals following scattering within the body part and by the marker at a plurality of receiving antennae of the microwave antenna array; and
generating an image of the body part showing an internal structure of the body part and the marker by processing the scattered microwave signals, so as to identify a region of interest within the body part relative to the position of the marker.

* * * * *